(12) United States Patent
McCord

(10) Patent No.: US 8,809,311 B2
(45) Date of Patent: *Aug. 19, 2014

(54) NUTRITIONAL SUPPLEMENTS

(76) Inventor: Darlene McCord, Coralville, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/853,908

(22) Filed: Aug. 10, 2010

(65) Prior Publication Data

US 2011/0034519 A1 Feb. 10, 2011

Related U.S. Application Data

(60) Provisional application No. 61/313,487, filed on Mar. 12, 2010, provisional application No. 61/235,203, filed on Aug. 19, 2009, provisional application No. 61/232,503, filed on Aug. 10, 2009.

(51) Int. Cl.

| A61K 45/06 | (2006.01) |
| A61K 31/198 | (2006.01) |
| A61K 31/401 | (2006.01) |
| A61K 31/455 | (2006.01) |
| A61K 31/05 | (2006.01) |
| A61K 31/4415 | (2006.01) |
| A61K 31/10 | (2006.01) |
| A61K 31/185 | (2006.01) |

(52) U.S. Cl.
CPC .......... *A61K 31/05* (2013.01); *A61K 45/06* (2013.01); *A61K 31/198* (2013.01); *A61K 31/401* (2013.01); *A61K 31/455* (2013.01); *A61K 31/4415* (2013.01); *A61K 31/10* (2013.01); *A61K 31/185* (2013.01)
USPC ........... 514/183; 514/345; 514/731; 514/562; 514/355; 514/578; 514/423; 514/711; 514/561; 568/763

(58) Field of Classification Search
CPC ... A61K 2300/00; A61K 31/05; A61K 31/10; A61K 31/185; A61K 31/198; A61K 31/401; A61K 31/4415; A61K 31/455; A61K 45/06
See application file for complete search history.

(56) References Cited

U.S. PATENT DOCUMENTS

| 4,871,550 A * | 10/1989 | Millman ............... 424/601 |
| 6,117,844 A | 9/2000 | Fredrickson |
| 6,165,475 A | 12/2000 | Crea et al. |
| 6,197,308 B1 | 3/2001 | Crea et al. |
| 6,309,652 B1 | 10/2001 | Aeschbach et al. |
| 6,358,542 B2 | 3/2002 | Cuomo et al. |
| 6,416,808 B1 | 7/2002 | Crea |
| 6,437,004 B1 | 8/2002 | Perricone |
| 6,746,706 B1 | 6/2004 | van der Boom et al. |
| 8,216,599 B2 | 7/2012 | Crea |
| 2001/0001817 A1* | 5/2001 | Humes .................. 604/892.1 |
| 2004/0101507 A1 | 5/2004 | Predovan |
| 2006/0257351 A1 | 11/2006 | Chiba |
| 2007/0065396 A1 | 3/2007 | Morariu |
| 2010/0113611 A1 | 5/2010 | Raederstorff et al. |
| 2013/0005682 A1 | 1/2013 | Raederstorff et al. |

FOREIGN PATENT DOCUMENTS

| EP | 0123637 A1 | 10/1984 |
| EP | 2070545 A1 | 6/2009 |
| JP | 2007119431 A | 5/2007 |
| WO | WO0036936 A2 | 6/2000 |
| WO | WO2004/032873 A2 | 4/2004 |
| WO | WO2006/020588 A1 | 2/2006 |
| WO | WO2008/006581 A2 | 1/2008 |
| WO | WO2008128629 A1 | 10/2008 |

OTHER PUBLICATIONS

Elisabet Miro-Casas et al, Clinical, Chemistry, 49:6, 945-952, 2003.*
Rietjens et al, Am. J. Phisiolo. Heart, Circ. Physiol. 292:H1931-H1936, 2007, published first in Dec. 2006.*
Pubmed, accessed Apr. 3, 2012.*
PCT Search Report for PCT/US2010/045049, dated Jan. 28, 2011.
Angelo, S. D., et al., Hydroxytyrosol, a natural antioxidant from olive oil, prevents protein damage induced by long-wave ultraviolet radiation in melanoma cells, Free Radical Biology & Medicine, 2005, 908-919, 38.
Fabiani, R., et al., Cancer chemoprevention by hydroxytyrosol isolated from virgin olive oil through G1 cell cycle arrest and apoptosis, European Journal of Cancer Prevention, 2002, 351-358, 11.
Ragione, F. D., et al., Hydroxytyrosol, a Natural Molecule Occuring in Olive Oil, Induces Cytochrome c-Dependent Apoptosis, Biochemical and Biophysical Research Communications, 2000, 733-739, 278.
Deiana, M., et al., Protective effect of hydroxytyrosol and its metabolite homovanillic alcohol on H2O2 induced lipid peroxidation in renal tubular epithelial cells, Food and Chemical Toxicology, 2008, 2984-2990, 46.
Fabiani, R., et al., Inhibition of Cell Cycle Progression by Hydroxytyrosol Is Associated with Upregulation of Cyclin-Dependent Protein Kinase Inhibitors p21^ WAF1/Cip1 and p27^ Kip1 and with Induction of Differentiation in HL60 Cells, The Journal of Nutrition: Nutrition and Disease, 2008, 42-48.
Guichard, C., et al., Dihydroxyphenylethanol induces apoptosis by activating serine/threonine protein phosphatase PP2A and promotes the endoplasmic reticulum stress response in human colon carcinoma cells, Carcinogenesis, 2006, 1812-1827, 27(9).
Liu, Z., et al., Hydroxytyrosol protects retinal pigment epithelial cells from acrolein-induced oxidative stress and mitochondrial dysfunction, Journal of Neurochemistry, 2007, 2690-2700, 103.
Manna, C., et al., Protective Effect of the Phenolic Fraction from Virgin Olive Oils against Oxidative Stress in Human Cells, Journal of Agricultural and Food Chemistry, 2002, 6521-6526, 50.

(Continued)

*Primary Examiner* — Wu-Cheng Winston Shen
*Assistant Examiner* — Jean Cornet
(74) *Attorney, Agent, or Firm* — McKee, Voorhees & Sease

(57) ABSTRACT

A process for improving the health of a subject, the process comprising orally administering a composition comprising hydroxytyrosol to the subject to provide the subject with a daily dose of about 0.1 to about 750 µg hydroxytyrosol per kg of body weight, and a dietary supplement in dosage unit form for oral administration, the dosage unit form comprising a composition containing about 1 microgram to about 50 milligrams hydroxytyrosol or an ester or salt thereof.

27 Claims, No Drawings

(56) References Cited

OTHER PUBLICATIONS

Dog, T. L., Menopause: a review of botanical dietary supplements, The American Journal of Medicine, 2005, 98S-108S, 118(12B).

Johnson, B. M., In Vitro Formation of Quinoid Metabolites of the Dietary Supplement *Cimicifuga racemosa* (Black Cohosh), Chemical Research in Toxicology, 2003, 838-846, 16(7).

Fernandez-Bolanos et al., Potential use of olive by-products Extraction of interesting organic compounds from olive oil waste, Grasas y Aceites, 2006, 95-106, 57(1).

Scalbert, Augustin, et al., "Absorption and metabolism of polyphenols in the gut and impact on health", Biomed Pharmacother 56 (2002), 276-282.

Visioli, Francesco, et al., "Antioxidant and Other Biological Activities of Olive Mill Waste Waters", J. Agric. Food Chem. 1999, 47, 3397-3401.

Haloui, Ehsen, et al., "Hydroxytyrosol and oleuropein from olive leaves: Potent anti-inflammatory and analgesic activities", Journal of Food, Agriculture & Environment, vol. 9 (3 & 4) (2011), 128-133.

Granados-Principal, Sergio, et al., "Hydroxytyrosol: from laboratory investigations to future clinical trials", Nutrition Reviews vol. 68 (4), 2010: 191-206.

Zhu, Lu, et al., "Hydroxytyrosol protects against oxidative damage by simultaneous activation of mitochondrial biogenesis and phase II detoxifying enzyme systems in retinal pigment epithelial cells", Journal of Nutritional Biochemistry (2010), pp. 1-10.

Zanichelli, Dario, et al., "Inhibition of *Staphylococcus aureus* by Oleuropein Is Mediated by Hydrogen Peroxide", Journal of Food Protections, vol. 68, No. 7, 2005, pp. 1492-1496.

Washington, Jennifer M., et al., "L-Proline induces differentiation of ES cells: a novel role for an amino acid in the regulation of pluripotent cells in culture", Am J Physiol Cell Physiol 298 (2010), C982-C992.

Tuck, Kellie L., et al., "Major phenolic compounds in olive oil: metabolism and health effects", Journal of Nutritional Biochemistry 13 (2002), 636-644.

Sarsour, Ehab H., et al., "Manganese Superoxide Dismutase Regulates a Metabolic Switch during the Mammalian Cell Cycle", 2012, pp. OF1-OF10.

Sarsour, Ehab H., et al., "MnSOD activity regulates hydroxytyrosol-induced extension of chronological lifespan", American Aging Association 2011, pp. 1-15.

Haber, C. Andrew, et al., "N-acetylcysteine and taurine prevent hyperglycemia-induced insulin resistance in vivo: possible role of oxidative stress", Am J Physiol Endocrinol Metab 285 (2003), E744-E753.

Victor, Victor M., et al., "N-acetylcysteine Protects Mice from Lethal Endotoxemia by Regulating the Redox State of Immune Cells", Free Radical Research, vol. 37 No. 9 (Sep. 2003), pp. 919-929.

Gonzalez-Correa, Jose Antonia, et al., "Neuroprotective effect of hydroxytyrosol acetate in rat brain slices subjected to hypoxia-reoxygenation", Neuroscience Letters 446 (2008), 143-146.

Vissers, Maud N., et al., "Olive Oil Phenols Are Absorbed in Humans", American Society for Nutritional Sciences, 2002, pp. 409-417.

Bisignano, Giuseppe, et al., "On the In-vitro Antimicrobial Activity of Leuropein and Hydroxytyrosol", J. Pharm. Pharmacol. 1999, 51: 971-974.

Webb, K.E., et al., "Peptide absorption: a review of current concepts and future perspectives", J Anim Sci 1992, 70: 3248-2357.

Pereira, Ana Paula, et al., "Phenolic Compounds and Antimicrobial Activity of Olive (*Olea europaea* L. Cv. Cobrancosa) Leaves", Molecules 2007, 12, 1153-1162.

Romani, Annalisa, et al., "Polyphenolic Content in Five Tuscany Cultivars of *Olea europaea* L.", J. Argic. Food Chem. 1999, 47, 964-967.

Walter, W.M., Jr., et al., "Preparation of Antimicrobial Compounds by Hydrolysis of Oleuropein from Green Olives", Applied Microbiology, Nov. 1973, vol. 26, No. 5, p. 773-776.

Capasso, Renato, et al., "Production of Glucose and Bioactive Aglycone by Chemical and Enymatic Hydrolysis of Purified Oeluropein from *Olea europea*", Applied Biochemistry and Biotechnology, vol. 61, 1996, pp. 365-377.

Matthews, D.M., et al.,. "Protein absorption", J. clin. Path., 24, Suppl. (Roy. Coll. Path.), 5, 2012, pp. 29-40.

EP0123637, Soto Lucien—English Abstract, 1984.

JP2007119431, Ichimaru Pharcos—English Abstract, 2005.

McCord, Darlene, PCT/US2010/045049 filed Jan. 12, 2012, "The Extended Europeans Search Report", dated Mar. 19, 2013.

* cited by examiner

NUTRITIONAL SUPPLEMENTS

CROSS-REFERENCE TO RELATED APPLICATIONS

This application claims priority to U.S. Provisional Application Ser. No. 61/232,503, filed Aug. 10, 2009, U.S. Provisional Application Ser. No. 61/235,203, filed Aug. 19, 2009, and U.S. Provisional Application Ser. No. 61/313,487, filed Mar. 12, 2010, each of which is incorporated herein by reference in its entirety.

FIELD OF THE INVENTION

The present invention relates to compositions comprising various vitamins, minerals, and anti-oxidants and methods for using these compositions for dietary or nutritional supplementation in, for example, subjects experiencing a diseased or physiologically stressful state or simply attempting to maintain good health.

BACKGROUND OF THE INVENTION

Nutrition plays a critical role in maintaining and restoring good health. When the body faces disease or physiological stress, proper nutrition plays an increasingly important role.

The characterization and marketing of naturally and non-naturally occurring antioxidants is receiving widespread attention in the everyday lives of many people today. Certain food groups having high levels of antioxidants are believed to provide prophylactic health benefits. Therefore, a myriad of supplements, herbal formulations, and herbal extracts are being marketed to consumers. In many cases, these compositions are promoted without solid scientific foundation. Currently, there is increased scientific interest in the role of anti-oxidants and the part they play in human health by reducing excessive free radicals.

There are two distinct mechanisms for cell death. Apoptosis is the result of "normal" or programmed cell death. Through this physiological process cells are routinely eliminated, giving balance to the proliferation of new cells. During apoptosis the outer membrane of the cell forms "bubbles" known as blebs. The content of the cells becomes incased in the blebs. The blebs separate from the cell and are digested by nearby cells or macrophages. This orderly process greatly reduces toxicity to surrounding cells.

Necrosis is the other form of cell death. This is not a programmed event and is known as "accidental" death. This pathological process occurs when cells are exposed to extreme stress, chemical insult, and resultant free radical damage. The early stages of necrosis involve a swelling of the cell called oncosis. During oncosis the cell and its organelles begin to swell due to an exchange in the cell's potassium to sodium ratios. Necrosis, after the oncosis stage, is an explosive event where the cells contents stream directly into the surrounding cells environment causing damage and an immune response. Controlling necrosis during the early oncosis stage is important. Up to this point, necrosis is a reversible event. The morphology of cells dying by necrosis centers on changes in the cell's permeability. Hengartner M O, The biochemistry of apoptosis. *Nature* 407: 770-776, 2000. Osmotic changes take place during an exchange of cytosol potassium and extracellular sodium. Early stage necrosis, known as oncosis, is characterized by the dilation or swelling of the cell and its organelles due to this exchange. Cell survival of this non-programmed event is dependent upon repairing the cell's membrane and stopping the flow of sodium ions into the cells interior. Repair of the cell's membrane and improvement in the cell's environment to more homeostatic conditions are paramount to survival Quiescence is the counterpart to proliferation and is a normal part of the cell cycle. The cell's replicative cycle involves a myriad of molecular events that occur during the quiescent state ($G_0$) and trigger the progression to the prereplicative ($G_1$) phase. Cosenza S C, Owen T A, Soprano D R, Soprano K J, Evidence That the Time of Entry into S is Determined by Events Occurring in Early $G_1$. *J Biological Chem* 263; 12751-12758; 1988. The $G_0$ phase represents not just the absence of signals for mitosis but an active repression of the genes needed for mitosis. This is an important distinction since cancer cells cannot enter $G_0$ and as a consequence become immortal.

During quiescence, a cell will reduce in size yet remain dynamic and metabolically active. A quiescent cell is more notable for what it does not do such as synthesize DNA. Coller H A, Sang L, Roberts J M, A New Description of Cellular Quiescence. *PLos Biology.* 4:0329-0349.2006. Quiescent cells are in a "state-of-readiness," like hibernation, waiting for the appropriate signal that it is once more time to move to the $G_1$ phase. Cells have a built-in conservation mechanism allowing it to survive for extended periods. Gray J V, Petsko G A, Johnston C, Ringe D, Singer R A, Werner-Washburne M, "Sleeping Beauty": in *Saccharomyces cerevisiae. Microbiology and Molecular Biology Reviews.* 68:2; 187-206:2004. If the cell remains in the quiescence state for an extended period, however, its ability to proliferate diminishes. Stated differently, the longer a cell stays in abnormal quiescence the more likely it becomes that the cell will die via necrosis. Just as with early stage necrosis, however, early quiescence is a reversible event that can be corrected by changing the cell's environment and reduction of free radicals in the cell's environment appears to be critical to the reversal process. See, e.g., Coller H A, Sang L, Roberts J M, 2006 A New Description of Cellular Quiescence. PLoS Biol 4(3): e83. doi:10.1371/journal.pbio.0040083.

SUMMARY OF THE INVENTION

Among the various aspects of the invention may be noted compositions for and methods of maintaining and restoring good health, compositions for and methods of treating an oxygen free radical-associated disease or condition, compositions for and methods of administration of an antioxidant and optionally, other dietary supplements to a subject in need thereof, and compositions for the inhibition and treatment of necrosis and extended quiescence that result in cellular necrosis instead of normal proliferation.

Briefly, therefore, the present invention is directed to compositions and methods for reversing damage to cells and, in particular, compositions and methods for promoting quiescence in at risk cells for the purpose of repairing aging and diseased cells. The compositions are in the form of dietary and nutritional supplements and are used by subjects experiencing a reduction in immune status or experiencing the effects of cellular failure associated with aging. For example, the compositions may reduce moles and skin tags in favor of normal skin cell proliferation.

Another aspect of the invention is a process for improving the health of a subject, the process comprising orally administering a composition comprising hydroxytyrosol to the subject to provide the subject with a daily dose of 0.05 to 0.75 micrograms of hydroxytyrosol per kilogram of body weight.

In another embodiment, the daily dose is about 0.1 to about 750 micrograms of hydroxytyrosol per kilogram of body weight.

Another aspect of the invention is a dietary supplement in dosage unit form suitable for oral administration. In one embodiment, the dosage unit form comprises a composition containing about 1 to about 50 micrograms hydroxytyrosol. In another embodiment, the dosage unit form comprises a composition containing about 1 microgram to about 50 milligrams hydroxytyrosol.

Other objects and features will be in part apparent and in part pointed out hereinafter.

DETAILED DESCRIPTION OF THE PREFERRED EMBODIMENTS

Surprisingly, it has been discovered that good health may be maintained or even improved by the administration of hydroxytyrosol in accordance with the present invention. In general, larger doses tend to produce greater effects, with the preferred dosage also depending, at least in part, upon weight, metabolism, individual body chemistry and the primary motivation for administering the composition. For example, if the hydroxytyrosol were being administered for a pre-existing condition the dosage may be significantly greater than if it were being administered as part of a preventative regimen.

In general, in one embodiment the dose of hydroxytyrosol administered to a person is about 0.05 to about 0.75 micrograms per kilogram of body weight. In one embodiment, the dose of hydroxytyrosol administered to a person is about 0.1 to about 0.5 micrograms per kilogram of body weight. For example, for a person having a body weight of about 75 kilograms, the dose of hydroxytyrosol is about 8-10 μg to about 30-40 μg, with the dosage depending upon whether the hydroxytyrosol is being administered as part of a preventive regimen or to treat a pre-existing condition (alone, or in combination with one or more other active pharmaceutical agents as part of a co-therapy regimen). As part of a preventative regimen, the average adult (i.e., about 75 kgs) may take about 9 μg of hydroxytyrosol per day whereas if a pre-existing condition is being treated, a higher dosage of 36 μg, for example, would be indicated.

Depending upon the route of administration and the purpose, greater doses of hydroxytyrosol may be administered. For example, significantly lesser amounts of hydroxytyrosol may be absorbed when the route of administration is oral as compared to parenteral or other forms of systemic administration. For oral delivery, therefore, the daily dose of hydroxytyrosol administered orally may be about 0.05 micrograms to about 750 micrograms per kilogram of body weight. By way of further example, in one embodiment, the daily dose of hydroxytyrosol administered orally to a person is about 1 to about 75 micrograms per kilogram of body weight. By way of further example, in one embodiment, the daily dose of hydroxytyrosol administered orally to a person is about 5 to about 50 micrograms per kilogram of body weight. By way of further example, in one embodiment, the daily dose of hydroxytyrosol administered orally to a person is about 10 micrograms to about 40 micrograms per kilogram of body weight. For example, in one embodiment, for a person having a body weight of about 75 kilograms, the daily dose of hydroxytyrosol is about 0.5 to about 50 milligrams, with the dosage depending upon whether the hydroxytyrosol is being administered as part of a preventive regimen or to treat a pre-existing condition (alone, or in combination with one or more other active pharmaceutical agents as part of a co-therapy regimen). By way of further example, the daily dose of hydroxytyrosol may be about 0.5 to about 5 milligrams. By way of further example, the daily dose of hydroxytyrosol may be about 0.75 to about 4 milligrams. By way of further example, the daily dose of hydroxytyrosol may be about 1 to about 3 milligrams. By way of further example, the daily dose of hydroxytyrosol may be about 1.25 to about 2.75 milligrams. As part of a preventative regimen, the average adult may take about 1.3 milligrams of hydroxytyrosol per day whereas if a pre-existing condition is being treated, a higher dosage of 2.6 milligrams, for example, would be indicated.

In certain embodiments, the hydroxytyrosol is administered parenterally and the daily dose is about 0.05 to about 10 micrograms per kilogram of body weight per day. In one embodiment, the daily dose of hydroxytyrosol parenterally administered to a person is about 0.1 to about 5 micrograms per kilogram of body weight per day. In another such embodiment, the daily dose of hydroxytyrosol parenterally administered to a person is about 0.1 to about 1 microgram per kilogram of body weight. In another such embodiment, the daily dose of hydroxytyrosol parenterally administered to a person is about 0.1 to about 1 micrograms per kilogram of body weight. For example, for a person having a body weight of about 75 kilograms, the parenterally administered daily dose of hydroxytyrosol may be about 5 micrograms to about 750 micrograms, with the dosage depending upon whether the hydroxytyrosol is being administered as part of preventive regimen or to treat a pre-existing condition (alone, or in combination with one or more other active pharmaceutical agents as part of a co-therapy regimen). By way of further example, the parenterally administered daily dose of hydroxytyrosol may be about 10 micrograms to about 500 micrograms. By way of further example, the parenterally administered daily dose of hydroxytyrosol may be about 10 micrograms to about 250 micrograms. As part of a preventative regimen, the average adult (i.e., about 75 kgs) may take about 10 micrograms of hydroxytyrosol per day whereas if a pre-existing condition is being treated, a higher dosage of 150 micrograms or less would be indicated.

In general, hydroxytyrosol may be administered in a single dose or multiple doses to achieve a target daily dose. For example, for certain embodiments the hydroxytyrosol is provided in a formulation that will provide, in a single daily dose, about 0.05 to about 0.75 micrograms of hydroxytyrosol per kilogram of body weight per day, preferably about 0.1 to about 0.5 micrograms of hydroxytyrosol per kilogram of body weight per day. Alternatively, for such embodiments the hydroxytyrosol is provided in a formulation that will provide, in two or more doses over the course of a day, about 0.05 to about 0.75 micrograms of hydroxytyrosol per kilogram of body weight per day, preferably about 0.1 to about 0.5 micrograms of hydroxytyrosol per kilogram of body weight per day. In general, for such embodiments a single dose in dosage unit form will contain at least about 1 microgram hydroxytyrosol but no more than about 50 micrograms hydroxytyrosol. More typically, for such embodiments a single dose in dosage unit form will contain will contain at least about 5 micrograms hydroxytyrosol but no more than about 40 micrograms hydroxytyrosol. For example, in one embodiment, a single dose in dosage unit form will contain at least 8 micrograms hydroxytyrosol, but no more than about 36 micrograms hydroxytyrosol.

As noted, greater amounts of hydroxytyrosol may be included in the dosage unit form when the intended route of administration is oral. For example, typical dosage forms for oral administration include tablets, pills, capsules, gelcaps, caplets, and the like. A single dose, therefore, may comprise a single tablet, pill, capsule, gelcap, caplet or the like, or two or more tablets, pills, capsules, gelcaps, caplets, and the like. In general, dosage forms for oral administration may contain 0.1 to 50 milligrams of hydroxytyrosol. For example, in one embodiment, the dosage unit form contains 1 to 25 milligrams hydroxytyrosol. By way of further example, in one embodiment, the dosage unit form contains 1 to 20 milligrams hydroxytyrosol. By way of further example, in one embodiment, the dosage unit form contains 1 to 15 milligrams hydroxytyrosol. By way of further example, in one embodiment, the dosage unit form contains 1 to 10 milligrams hydroxytyrosol. By way of further example, in one embodiment the dosage unit form contains 2.5 to 7.5 milligrams hydroxytyrosol. In some embodiments, the dosage unit form contains somewhat less, e.g., 0.1 to 5 milligrams of hydroxytyrosol. For example, dosage forms for oral administration may contain 0.5 to 4 milligrams of hydroxytyrosol. By way of further example, dosage forms for oral administration may contain 0.75 to 3 milligrams of hydroxytyrosol. By way of further example, dosage forms for oral administration may contain 1 to 3 milligrams of hydroxytyrosol. By way of further example, dosage forms for oral administration may contain 1.25 to 2.75 milligrams of hydroxytyrosol.

In addition to hydroxytyrosol, the compositions of the present invention may contain N-acetyl cysteine and/or an additional component that improves the health or viability of cells. Such additional components, for example, may include other antioxidants, vitamins, minerals, and/or amino acids. Non-limiting examples of other antioxidants include ascorbic acid (vitamin C) and its salts, ascorbyl esters of fatty acids, ascorbic acid derivatives (e.g., magnesium ascorbyl phosphate, sodium ascrobyl phosphate, and ascorbyl sorbate), EGCG, oleuropein, tocopherol (vitamin E), tocopherol sorbate, tocopherol acetate, other esters of tocopherol, tyrosol, butylated hydroxy benzoic acids and their salts, gallic acid and its alkyl esters such as propyl gallate, uric acid and its salts and alkyl esters, sorbic acid and its salts, lipoic acid, amines (e.g., N,N-diethylhydroxylamine and amino-guanidine), sulfhydryl compounds (e.g., glutathione), dihydroxy fumaric acid and it salts, glycine pidolate, arginine pilolate, nordihydroguaiaretic acid, bioflavinoids, curcumin, lysine, methionine, proline, superoxide dismutase, resveratrol, and other polyphenols. In another embodiment, the composition comprises hydroxytyrosol, N-acetyl cysteine, and one or more of cystine, cystine derivatives, vitamin C, tannic acid, vitamin E, vitamin E derivatives, catechin, niacin, unsaturated fatty acids, vitamin P, vitamin Q, glutathione, isoflavones, guava, selenium, oleuropein or other polyphenol(s). In one embodiment, the composition comprises hydroxytyrosol, N-acetyl cysteine and one or more of glycine, L-taurine, L-proline, niacinamide (vitamin B3), pyridoxine (vitamin B6), and methylsulfonylmethane.

In one embodiment, the composition contains non-amino acid additives such as aloe vera, oat extract, hyaluronic acid, betaglucan or like substance to provide glycosaminoglycans for extracellular matrix protection. Vitamins may be additives, especially vitamins A/D3, all B vitamins and all stable C vitamins. Omega 3 and 6 fatty acids will be balanced with the greater percentage being 3. In one embodiment, the composition may contain other antioxidants, anti-inflammatory agents and tissue repair ingredients known to have wound healing benefits. For example, in one embodiment, the composition contains olive leaf extract, vitamin A/D3, Vitamin C, and essential fatty acids from olive oil, canola oil, safflower oil, borrage oil and sunflower oil. Also preferably, olive leaf extract is present in the composition of the present invention.

In one embodiment, the composition contains N-acetyl cysteine and hydroxytyrosol and the weight ratio of N-acetyl cysteine to hydroxytyrosol to between 1:1 and 50:1, respectively. In one embodiment, the composition contains N-acetyl cysteine and hydroxytyrosol and the weight ratio of N-acetyl cysteine to hydroxytyrosol is between 10:1. and 30:1, respectively. For example, in one such embodiment, the composition contains N-acetyl cysteine and hydroxytyrosol and the weight ratio of N-acetyl cysteine to hydroxytyrosol is between 20:1 and 25:1, respectively.

In one embodiment, the composition contains glycine and hydroxytyrosol and the weight ratio of glycine to hydroxytyrosol to between 1:1 and 50:1, respectively. In one embodiment, the composition contains glycine and hydroxytyrosol and the weight ratio of glycine to hydroxytyrosol is between 30:1 and 40:1, respectively. For example, in one such embodiment, the composition contains glycine and hydroxytyrosol and the weight ratio of glycine to hydroxytyrosol is about 35:1, respectively.

In one embodiment, the composition contains L-taurine and hydroxytyrosol and the weight ratio of L-taurine to hydroxytyrosol to between 1:1 and 50:1, respectively. In one embodiment, the composition contains L-taurine and hydroxytyrosol and the weight ratio of L-taurine to hydroxytyrosol is between 20:1 and 50:1, respectively. In one embodiment, the composition contains L-taurine and hydroxytyrosol and the weight ratio of L-taurine to hydroxytyrosol is between 30:1 and 40:1, respectively. For example, in one such embodiment, the composition contains L-taurine and hydroxytyrosol and the weight ratio of L-taurine to hydroxytyrosol is about 35:1, respectively.

In one embodiment, the composition contains L-proline and hydroxytyrosol and the weight ratio of L-proline to hydroxytyrosol to between 1:1 and 20:1, respectively. In one embodiment, the composition contains L-proline and hydroxytyrosol and the weight ratio of L-proline to hydroxytyrosol is between 1:1 and 10:1, respectively. In one embodiment, the composition contains L-proline and hydroxytyrosol and the weight ratio of L-proline to hydroxytyrosol is between 1:1 and 5:1, respectively.

In one embodiment, the composition contains methylsulfonylmethane and hydroxytyrosol and the weight ratio of methylsulfonylmethane to hydroxytyrosol to between 1:1 and 30:1, respectively. In one embodiment, the composition contains methylsulfonylmethane and hydroxytyrosol and the weight ratio of methylsulfonylmethane to hydroxytyrosol is between 5:1 and 25:1, respectively. In one embodiment, the composition contains methylsulfonylmethane and hydroxytyrosol and the weight ratio of methylsulfonylmethane to hydroxytyrosol is between 10:1 and 20:1, respectively.

In one embodiment, the composition contains niacinamide and hydroxytyrosol and the weight ratio of niacinamide to hydroxytyrosol to between 1:1 and 10:1, respectively. In one embodiment, the composition contains niacinamide and hydroxytyrosol and the weight ratio of niacinamide to hydroxytyrosol is between 1:1 and 5:1, respectively. In one embodiment, the composition contains niacinamide and hydroxytyrosol and the weight ratio of niacinamide to hydroxytyrosol is between 1:1 and 2:1, respectively.

In one embodiment, the composition contains pyridoxine and hydroxytyrosol and the weight ratio of pyridoxine to hydroxytyrosol to between 1:1 and 10:1, respectively. In one embodiment, the composition contains pyridoxine and hydroxytyrosol and the weight ratio of pyridoxine to hydroxytyrosol is between 1:1 and 5:1, respectively. In one embodiment, the composition contains pyridoxine and hydroxytyrosol and the weight ratio of pyridoxine to hydroxytyrosol is between 1:1 and 2:1, respectively.

In one preferred embodiment, the composition of the present invention contains hydroxytyrosol, N-acetyl cysteine and optionally one or more of glycine, L-taurine, L-proline, niacinamide (B3), pyridoxine (B6), and methylsulfonylmethane. In one example of this embodiment, the weight ratio N-acetyl cysteine to hydroxytyrosol is between 1:1 and 50:1, respectively, the weight ratio glycine to hydroxytyrosol is between 1:1 and 50:1, respectively, the weight ratio of L-taurine to hydroxytyrosol is between 1:1 and 50:1, respectively, the weight ratio of L-proline to hydroxytyrosol is between 1:1 and 20:1, respectively, the weight ratio of niacinamide to hydroxytyrosol is between 1:1 and 10:1, respectively, the weight ratio of pyridoxine to hydroxytyrosol is between 1:1 and 10:1, and the weight ratio of methylsulfonylmethane to hydroxytyrosol is between 1:1 and 30:1. In another example of this embodiment, the weight ratio N-acetyl cysteine to hydroxytyrosol is between 10:1 and 30:1, respectively, the weight ratio glycine to hydroxytyrosol is between 30:1 and 40:1, respectively, the weight ratio of L-taurine to hydroxytyrosol is between 20:1 and 50:1, respectively, the weight ratio of L-proline to hydroxytyrosol is between 1:1 and 10:1, respectively, the weight ratio of niacinamide to hydroxytyrosol is between 1:1 and 5:1, respectively, the weight ratio of pyridoxine to hydroxytyrosol is between 1:1 and 5:1, and the weight ratio of methylsulfonylmethane to hydroxytyrosol is between 10:1 and 30:1. In another example of this embodiment, the weight ratio N-acetyl cysteine to hydroxytyrosol is between 20:1 and 25:1, respectively, the weight ratio glycine to hydroxytyrosol is between 30:1 and 40:1, respectively, the weight ratio of L-taurine to hydroxytyrosol is between 30:1 and 40:1, respectively, the weight ratio of L-proline to hydroxytyrosol is between 1:1 and 5:1, respectively, the weight ratio of niacinamide to hydroxytyrosol is between 1:1 and 2:1, respectively, the weight ratio of pyridoxine to hydroxytyrosol is between 1:1 and 2:1, and the weight ratio of methylsulfonylmethane to hydroxytyrosol is between 10:1 and 20:1.

In each of the aforementioned embodiments, the components of the composition of the present invention may optionally be present in the form of an ester or a physiologically/pharmaceutically acceptable salt. Exemplary esters include the mono-, di- and triesters of hydroxytyrosol with (un)saturated carbonic acids R—COON, whereby R is an alkyl or alkenyl chain having 2 to 22 carbon atoms. Exemplary pharmaceutically acceptable salts refers to salts prepared from pharmaceutically acceptable non-toxic acids, including inorganic salts and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and other pharmaceutically acceptable salts as provided in Stahl and Wermuth "Pharmaceutical Salts Properties, Selection, and Use", 1st Ed, Wiley-VCH, 374 (2002). Thus, for example, the hydroxytyrosol may be provided as hydroxytyrosol acetate which releases hydroxytyrosol in the stomach or intestine.

For use in the composition of the present invention, hydroxytyrosol may be derived from natural sources or prepared by chemical synthesis. For example, the hydroxytyrosol may be obtained as an extract of, or otherwise derived from, olive leaves, olive fruits and vegetation water of olive oil production. When obtained as an extract, for example, of olive leaves, the extract will contain hydroxytyrosol, tyrosol, oleuropein, and other polyphenols. In one preferred embodiment, the hydroxytyrosol is obtained as an olive leaf extract of *Olea europaea*.

Oxygen radical absorbance capacity ("ORAC") is a method of measuring antioxidant capacities in biological samples (Wu, X., et al., Journal of Agricultural and Food Chemistry 52:4026-4037 (2004). The assay measures the oxidative degradation of the fluorescent molecule (either beta-phycoerythrin or fluorescein) after being mixed with free radical generators such as azo-initiator compounds. Antioxidants inhibit the free radical range damage to the fluorescent compound and prevent the reduction in fluorescence and the results are compared to the known antioxidant Trolox® with the ORAC results expressed as Trolox® equivalents (6-Hydroxy-2,5,7,8-tetramethylchroman-2-carboxylic Acid; TE) per gram of sample. One ORAC unit is defined as micromoles of Trolox Equivalence (TE) per gram or liter of the sample.

Taking into account the dose of hydroxytyrosol, other components of the hydroxytyrosol containing composition, and other components of a daily diet, it is also preferred that the total oxygen radical absorbance capacity, ORAC, consumed by a person, not exceed about 6,000 Trolox equivalents (TE) per day. In one embodiment, the total ORAC value is at least about 2,000 and less than 6,000 TE per day. In a more preferred embodiment, the daily dose of hydroxytyrosol is coordinated with the subject's diet to provide the subject with a daily total oxygen radical absorbance capacity of less than 5,500 TE per day. In a more preferred embodiment, the daily dose of hydroxytyrosol is coordinated with the subject's diet to provide the subject with a daily total oxygen radical absorbance capacity of about 3,000 to about 5,000 TE per day. In general, it is preferred that the daily dose of hydroxytyrosol that is systemically bioavailable to the subject may constitute about 10% to about 75% of this total; stated differently it is preferred that the daily dose. More typically, the hydroxytyrosol (or an ester or salt thereof) may constitute about 20% to about 60% of this total. In certain embodiments, the hydroxytyrosol (or an ester or salt thereof) may constitute about 30% to about 50% of this total.

As previously noted, the route of administration may affect the rate and extent of absorption of hydroxytyrosol. Taking this into account, i.e., taking into account the fraction of an administered dose that is not absorbed or for whatever reason is not systemically bioavailable to the subject, it is generally preferred that the administered dose provide the subject with at least about 100 but less than about 6,000 TE of systemically bioavailable hydroxytyrosol per day. In general, it is preferred that the administered dose provide the subject with at least about 250 TE of systemically bioavailable hydroxytyrosol per day. In certain embodiments, it is preferred that the administered dose provide the subject with at least about 500 TE of systemically bioavailable hydroxytyrosol per day. In other embodiments, it is preferred that the administered dose provide the subject with at least about 750 TE of systemically bioavailable hydroxytyrosol per day. Typically, however, the administered dose will provide the subject with less than about 5,000 TE of systemically bioavailable hydroxytyrosol per day. More typically, the administered dose will provide the subject with less than about 4,000 TE of systemically bioavailable hydroxytyrosol per day. In some embodiments, the administered dose will provide the subject with less than about 3,000 TE of systemically bioavailable hydroxytyrosol per day. In certain embodiments, the administered dose will provide the subject with less than about 2,500 TE of systemically bioavailable hydroxytyrosol per day. By way example, therefore, in one such embodiment, the administered dose provides the subject with about 250 to 4,000 TE of systemically bioavailable hydroxytyrosol per day. By way of further example, in one such embodiment, the administered dose provides the subject with about 500 to 3,500 TE of systemically bioavailable hydroxytyrosol per day. By way of further example, in one such embodiment, the administered dose provides the subject with about 750 to 3,000 TE of systemically bioavailable hydroxytyrosol per day. By way of further example, in one such embodiment, the administered dose provides the subject with about 750 to 2,000 TE of systemically bioavailable hydroxytyrosol per day.

Compositions containing hydroxytyrosol may be formulated in any conventional manner. Proper formulation is dependent upon the route of administration chosen. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: hydroxytyrosol concentration and intended bioavailability; the disease, disorder or condition being treated with the composition; the subject, his or her age, size and general condition; and the route of administration. Suitable carriers are readily determined by one of ordinary skill in the art (see, for example, J. G. Nairn, in: Remington's Pharmaceutical Science (A. Gennaro, ed.), Mack Publishing Co., Easton, Pa., (1985), pp. 1492-1517, the contents of which are incorporated herein by reference).

In general, oral routes of administration are preferred. For oral administration, the hydroxytyrosol containing compositions are preferably formulated as tablets, dispersible powders, pills, capsules, gelcaps, caplets, gels, liposomes, granules, solutions, suspensions, emulsions, syrups, elixirs, troches, dragees, lozenges, or any other dosage form which can be administered orally. Techniques and compositions for making oral dosage forms useful in the present invention are described in the following references: 7 Modern Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976).

The compositions of the invention for oral administration comprise an effective amount of hydroxytyrosol in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques; e.g., to delay disintegration and absorption is administered systemically, in a single dose or multiple doses.

The hydroxytyrosol containing compositions of the present invention may also be preferably formulated for parenteral administration, e.g., formulated for injection via intravenous, intraarterial, subcutaneous, rectal, subcutaneous, intramuscular, intraorbital, intracapsular, intraspinal, intraperitoneal, or intrasternal routes. The compositions of the invention for parenteral administration comprise an effective amount of hydroxytyrosol in a pharmaceutically acceptable carrier. Dosage forms suitable for parenteral administration include solutions, suspensions, dispersions, emulsions or any other dosage form which can be administered parenterally. Techniques and compositions for making parenteral dosage forms are known in the art.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methylpyrrolidinone, pluronic 60, polyoxyethylene sorbitol oleic polyesters such as poly(ethoxylated)30-60 sorbitol poly(oleate)2-4, poly(oxyethylene)15-20 monooleate, poly(oxyethylene)15-20 mono 12-hydroxystearate, and poly(oxyethylene)15-20 mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a C4-C22 fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Without seeking to limit the invention or to be bound by any particular theory, it is believed that promoting or maintaining cell health of the cells of a mammal by administering a therapeutically effective amount of a composition of the present invention may act through one or more of the following mechanisms: a) treating or preventing oncosis or extended quiescence of the cells; b) maintaining or increasing the amount of adenosine triphosphate (ATP) in the extracellular spaces within a mammal; c) repairing the cell membranes within a mammal; d) restoring the normal osmotic balance across the cell membranes or stopping the flow of sodium ions in the cells; e) activating quiescence in cells that have not moved normally through the cell cycle; f) protecting against free radical damage to the cell, its organelles and the extracellular spaces; g) protecting against cellular necrosis during the pre-lethal stages; h) restores the cellular balance between NAD and NADH in favor of NAD; i) activates the FOX03a protein necessary to place a cell into quiescence during the cellular repair process; and j) restores endogenous MnSOD necessary for mitochondrial repair.

In the present invention, an "effective amount" or "therapeutically effective amount" of a compound or of a composition of the present invention is that amount of such compound and/or composition that is sufficient to effect beneficial or desired results as described herein. In terms of treatment of a mammal, e.g., a human patient, an "effective amount" is an amount sufficient to treat, reduce, manage, palliate, ameliorate, or stabilize a condition, such as a non-congenital oncosis or extended quiescence of the cells of a mammal, or both, as compared to the absence of the compound or composition.

Having described the invention in detail, it will be apparent that modifications and variations are possible without departing the scope of the invention defined in the appended claims. Furthermore, it should be appreciated that all examples in the present disclosure are provided as non-limiting examples.

Example 1

Rheumatoid Arthritis Case-Study

Rheumatoid arthritis (RA) is a chronic disease that affects approximately 2.1 million people in the United States, according to the Arthritis Foundation, with 70 percent of the patients being women. Worldwide about 2 percent of the population has RA. It is characterized by pain, stiffness and swelling in the joints. RA is unlike osteoarthritis (OA), which is associated with age, obesity and injury. RA occurs when the body's immune system fails to protect the joint tissue from bacteria and viruses. This immune system failure leads to painful and swollen joints that may eventually cause permanent disability.

In a research survey done for the Arthritis Foundation that included 500 RA patients and 200 physicians, it was found that more than two-thirds claimed the disease prevented them from living a fully productive life. Many felt that it impeded their social life and led to a feeling of loneliness and isolation. Study highlights include:

81 percent felt they were no longer in control of their lives
    80 percent found small tasks like getting dressed became a major effort
    70 percent gave up exercise and household chores at their worst
    66 percent claimed getting out of bed was more difficult
    50 percent gave up social activities with family and friends In a study authored by Dr. Roxabella Torres, Dr. Fred Wolfe and Kaleb Michaud and presented at the annual American College of Rheumatology (ARC) Scientific Meeting it was found that more than 40 percent of RA patients had difficulty affording their medical care. The study showed:

37.3 percent did not buy drugs
    32.3 percent reported having moderate difficulty paying for care
    8.2 percent had great difficulty paying for care
    7.1 percent skipped surgery because of costs A 59 year-old Caucasian woman has been suffering from rheumatoid arthritis, with inflammatory symptoms and patellofemoral syndrome for the last ten years. Pain became unbearable for about three months, temporarily tapered off, but then returned. She began experiencing pain daily, with more intensity at night.

She was originally prescribed piroxicam, and later prescribed nabumetone, which are commonly prescribed for osteoarthritis and rheumatoid arthritis. She also takes part in occupational therapy and paraffin wax treatments of the hands.

Her symptoms made it difficult to move and she especially suffered from severe back pain. It was an effort to just get out of bed. Most days it was very difficult to get to sleep because her hands and legs would ache. Routinely, the pain in her legs would wake her during the night and it limited the amount of time she could spend outside gardening, tending flowers, and exercising during the day.

She then began taking four capsules of formula 5260C daily by mouth everyday, two in the morning and two at bedtime. Each capsule contains olive leaf extract (hydroxytyrosol 7% standardized), supplemented with glycine, L-taurine, N-acetyl-L-cysteine, methylsulfonylmethane, L-proline, niacinamide, and pyridoxine HCl and provided her with a daily dose of 21 mg. hydroxytyrosol. No other changes were instituted in diet or lifestyle.

Within two weeks the patient was able to get out of bed without pain, and get through the day with optimism. At week three, the patient was able to use stairs and get up and down from the floor and experienced a substantial reduction in pain. At week four, the patient was able to go outside and play with the grand children and participate in family activities that she had not experienced in several years.

The most promising aspect of the trial was the cost savings and improved quality of life experienced by the patient due to the cessation of her prescription medications. Within four weeks the patient was able to discontinue the following medications:

ACETAMINOPHEN (EXTRA STRENGTH): TABLET, 500 MG/1 TAB strength, take 1000 mg ORAL—prn CALCIUM CARBONATE (CALCIUM): TABLET, 600 MG/1 TAB strength, take 600 mg ORAL—BID FEXOFENADINE: TABLET, 60 MG/1 TAB strength, take 60 mg ORAL—BID prn AR NABUMETONE: TABLET, 500 MG/1 TAB strength, take 1-2 tab ORAL—BID prn tenosynovitis.

According to the patient: "I noticed a difference in the way I feel since using the trial product. I noticed that I was able to kneel and play with my grandkids without great effort in getting up from the floor and I stopped requiring the daily routine of [nabumetone] to get going or to quiet my pain before going to bed. My hip pain is gone and it is no effort to climb stairs as it was before. I truly feel half my age! It's been a true miracle for me, especially thinking back to those days of lying in bed knowing how bad I hurt and wondering how much more pain my future would hold."

Patient has meet with her physicians and the findings of this study are part of her medical records.

REFERENCES

1. J Rheumatol 2000 October; 27(10):2343-6
2. J Biol Chem 2000 Jan. 14; 275(2):721-4
3. Am J Clin Nutr 2000 January; 71(Suppl):3495-51S
4. J Indian Rheumatol Assoc 2004; 12:139-42
5. J Am Coll Nutr 2003 August; 22(4):311-15
6. J Hum Nutr Dietet 2003 16:97-109

Example 2

Hepatitis C

Hepatitis C is an acute and chronic liver disease caused by infection with the Hepatitis C virus. In the United States, the virus is responsible for affecting more than 3 million people or 1.6% of the population. Approximately 17,000 new cases in the US are reported each year.

The disease is characterized by fever, fatigue, malaise, nausea, vomiting, abdominal pain, jaundice, grey-colored bowel movements, dark urine and joint pain. The physical condition can also lead to emotional stress. Statistics show that up to 85% of people with the infection develop lifelong illness. Of these people, 60-70% will develop chronic liver disease; 10-20% will develop cirrhosis; 1-5% will develop liver cancer, according to the Centers for Disease Control and Prevention.

A 56 year-old Caucasian woman has suffered from hepatitis C for more than 25 years. She was treated with interferon for 12 months more than 10 years ago. Several years ago, she received 15 months of treatments with interferon and ribavirin, resulting in severe anemia, which required weekly injections to manage. Because of the disease, she has also experienced problems with low energy, insomnia and significant pain, all symptoms that have interfered with normal daily functions.

At the commencement of the study, the patient was unable to get out of bed and had difficulty with breathing, which was painful. She was unable to perform daily chores including cooking, cleaning and yard work. These conditions required external care and supervision. The patient was not on prescription medicines at the time the trial commenced and remains prescription drug free.

She then began taking four capsules of formula 5260C daily by mouth everyday, two in the morning and two at bedtime. Each capsule contains olive leaf extract (hydroxytyrosol 7% standardized), supplemented with glycine, L-taurine, N-acetyl-L-cysteine, methylsulfonylmethane, L-proline, niacinamide, and pyridoxine HCl and provided her with a daily dose of 21 mg. hydroxytyrosol. No other changes were instituted in diet or lifestyle.

Within one week there were dramatic results in the patient's ability to breath without pain, get out of bed and get through the day with optimism. At week two the patient was cooking for herself, had an improved mental outlook and experienced a substantial reduction in pain. At week three the patient was able to go outside and mow the lawn and rake leaves, activities that she had not experienced in more than a year.

Six weeks into the treatment the patient felt well enough to plan a lifelong dream trip to Tanzania. At week eight she left for a two-week vacation in Tanzania and was able to complete the trip without issue. The trip included daily activities of walking and hiking. The patient has returned and continues to improve. She has returned to work part time.

According to the patient: "I feel that I have a lot more energy and can stand up straight. My pain has decreased, and my quality of sleep increased. I have been told that I act more like my 'old self'. In addition, she reports the added benefits of less hair loss and improved outlook on life. "I feel optimistic about the future." Though hepatitis C has become a chronic disease for her, she now feels "better than I ever thought possible."

Patient has meet with her physicians and the findings of this study are part of her medical records.

REFERENCES

1. U.S. Department of Health and Human Services, National Institute of Diabetes and Digestive and Kidney Diseases, available at digestive.niddk.nih.gov/ddiseases/pubs/chronichepc.
2. Centers for Disease Control and Prevention available at www.cdc.gov/hepatitis

What is claimed is:

1. A dietary supplement in dosage unit form for oral administration, the dosage unit form comprising:
   a composition containing about 0.5 to about 50 milligrams hydroxytyrosol or an ester or salt thereof, N-acetyl cysteine, glycine, L-taurine, L-proline, methylsulfonylmethane, niacinamide, and pyridoxine,
   wherein the hydroxytyrosol or an ester or salt thereof comprises hydroxytyrosol and oleuropein,
   wherein the weight ratio of N-acetyl cysteine to hydroxytyrosol is between 1:1 and 50:1,
   wherein the weight ratio of glycine to hydroxytyrosol is between 1:1 and 50:1,
   wherein the ratio of L-taurine to hydroxytyrosol is between 1:1 and 50:1, and
   wherein the weight ratio of L-proline to hydroxytyrosol is between 1:1 and 20:1.

2. The dietary supplement of claim 1, wherein the dosage unit form comprises 0.5 milligrams to 5 milligrams hydroxytyrosol or an ester or salt thereof.

3. The dietary supplement of claim 1, wherein the dosage unit form comprises 1 to 25 milligrams hydroxytyrosol or an ester or salt thereof.

4. The dietary supplement of claim 1 wherein the dosage unit form comprises 1 to 20 milligrams hydroxytyrosol or an ester or salt thereof.

5. The dietary supplement of claim 1 wherein the dosage unit form comprises 1 to 15 milligrams hydroxytyrosol or an ester or salt thereof.

6. The dietary supplement of claim 1 wherein the dosage unit form comprises 1 to 10 milligrams hydroxytyrosol or an ester or salt thereof.

7. The dietary supplement of claim 1 wherein the dosage unit form comprises 2.5 to 7.5 milligrams hydroxytyrosol or an ester or salt thereof.

8. The dietary supplement of claim 1 wherein the weight ratio of N-acetyl cysteine to hydroxytyrosol is between 10:1 and 30:1, respectively.

9. The dietary supplement of claim 8 wherein the weight ratio of N-acetyl cysteine to hydroxytyrosol is between 20:1 and 25:1, respectively.

10. The dietary supplement of claim 1 wherein the weight ratio of glycine to hydroxytyrosol is between 30:1 and 40:1, respectively.

11. The dietary supplement of claim 10 wherein the weight ratio of glycine to hydroxytyrosol is about 35:1, respectively.

12. The dietary supplement of claim 1 wherein the ratio of L-taurine to hydroxytyrosol is between 20:1 and 50:1, respectively.

13. The dietary supplement of claim 12 wherein the weight ratio of L-taurine to hydroxytyrosol is between 30:1 and 40:1, respectively.

14. The dietary supplement of claim 1 wherein the weight ratio of L-proline to hydroxytyrosol is between 1:1 and 10:1, respectively.

15. The dietary supplement of claim 14 wherein the weight ratio of L-proline to hydroxytyrosol is between 1:1 and 5:1, respectively.

16. The dietary supplement of claim 1 wherein the weight ratio of methylsulfonylmethane to hydroxytyrosol is between 1:1 and 30:1, respectively.

17. The dietary supplement of claim 16 wherein the weight ratio of methylsulfonylmethane to hydroxytyrosol is between 10:1 and 20:1, respectively.

18. The dietary supplement of claim 1 wherein the weight ratio of niacinamide to hydroxytyrosol is between 1:1 and 10:1, respectively.

19. The dietary supplement of claim 18 wherein the weight ratio of niacinamide to hydroxytyrosol is between 1:1 and 2:1, respectively.

20. The dietary supplement of claim 1 wherein the weight ratio of pyridoxine to hydroxytyrosol is between 1:1 and 10:1, respectively.

21. The dietary supplement of claim 20 wherein the weight ratio of pyridoxine to hydroxytyrosol is between 1:1 and 2:1, respectively.

22. The dietary supplement of claim 1 wherein weight ratio N-acetyl cysteine to hydroxytyrosol is between 10:1 and 30:1, respectively, the weight ratio glycine to hydroxytyrosol is between 30:1 and 40:1, respectively, the weight ratio of L-taurine to hydroxytyrosol is between 20:1 and 50:1, respectively, the weight ratio of L-proline to hydroxytyrosol is between 1:1 and 10:1, respectively, the weight ratio of niacinamide to hydroxytyrosol is between 1:1 and 10:1, respectively, the weight ratio of pyridoxine to hydroxytyrosol is between 1:1 and 10:1, and the weight ratio of methylsulfonylmethane to hydroxytyrosol is between 1:1 and 30:1.

23. The dietary supplement of claim 1 wherein weight ratio N-acetyl cysteine to hydroxytyrosol is between 20:1 and 25:1, respectively, the weight ratio glycine to hydroxytyrosol is between 30:1 and 40:1, respectively, the weight ratio of L-taurine to hydroxytyrosol is between 30:1 and 40:1, respectively, the weight ratio of L-proline to hydroxytyrosol is between 1:1 and 5:1, respectively, the weight ratio of niacinamide to hydroxytyrosol is between 1:1 and 2:1, respectively, the weight ratio of pyridoxine to hydroxytyrosol is between 1:1 and 2:1, and the weight ratio of methylsulfonylmethane to hydroxytyrosol is between 10:1 and 20:1.

24. The dietary supplement of claim 1 wherein the dosage unit form provides about 250 to 4,000 TE of systemically bioavailable hydroxytyrosol.

25. The dietary supplement of claim 24 wherein weight ratio N-acetyl cysteine to hydroxytyrosol is between 20:1 and 25:1, respectively, the weight ratio glycine to hydroxytyrosol is between 30:1 and 40:1, respectively, the weight ratio of L-taurine to hydroxytyrosol is between 30:1 and 40:1, respectively, the weight ratio of L-proline to hydroxytyrosol is between 1:1 and 5:1, respectively, the weight ratio of niacinamide to hydroxytyrosol is between 1:1 and 2:1, respectively, the weight ratio of pyridoxine to hydroxytyrosol is between 1:1 and 2:1, and the weight ratio of methylsulfonylmethane to hydroxytyrosol is between 10:1 and 20:1.

26. The dietary supplement of claim 1 wherein the dosage unit form provides about 500 to 3,500 TE of systemically bioavailable hydroxytyrosol per day.

27. The dietary supplement of claim 26 wherein weight ratio N-acetyl cysteine to hydroxytyrosol is between 20:1 and 25:1, respectively, the weight ratio glycine to hydroxytyrosol is between 30:1 and 40:1, respectively, the weight ratio of L-taurine to hydroxytyrosol is between 30:1 and 40:1, respectively, the weight ratio of L-proline to hydroxytyrosol is between 1:1 and 5:1, respectively, the weight ratio of niacinamide to hydroxytyrosol is between 1:1 and 2:1, respectively, the weight ratio of pyridoxine to hydroxytyrosol is between 1:1 and 2:1, and the weight ratio of methylsulfonylmethane to hydroxytyrosol is between 10:1 and 20:1.

* * * * *